(12) United States Patent
Knutson (10) Patent No.: US 7,806,688 B2
(45) Date of Patent: Oct. 5, 2010

(54) SOFT POLYMER DENTAL SHEET AND PROCESSES THEREFOR

(76) Inventor: Eric J. Knutson, 5815 Granite Hills Dr., Granite Bay, CA (US) 95746

( * ) Notice: Subject to any disclaimer, the term of this patent is extended or adjusted under 35 U.S.C. 154(b) by 265 days.

(21) Appl. No.: 11/636,153

(22) Filed: Dec. 9, 2006

(65) Prior Publication Data

US 2008/0138771 A1    Jun. 12, 2008

(51) Int. Cl.
*A61C 9/00* (2006.01)
(52) U.S. Cl. .................................................... 433/71
(58) Field of Classification Search ............... 433/68, 433/69, 70, 71
See application file for complete search history.

(56) References Cited

U.S. PATENT DOCUMENTS

| | | | | |
|---|---|---|---|---|
| 3,218,374 | A | 11/1965 | Perbohner et al. | 264/17 |
| 4,003,132 | A | 1/1977 | Beck | 32/17 |
| 4,472,140 | A | 9/1984 | Lustig | 433/38 |
| 4,547,155 | A * | 10/1985 | Adler | 433/70 |
| 4,689,010 | A | 8/1987 | Wolfe | 433/38 |
| 4,856,993 | A | 8/1989 | Maness | 433/68 |
| 5,102,335 | A | 4/1992 | Getz | 433/38 |
| 5,316,474 | A | 5/1994 | Robertson | 433/38 |
| 5,381,799 | A | 1/1995 | Hamilton | 600/590 |
| 5,403,885 | A | 4/1995 | Voigt | 542/731 |
| 5,636,985 | A | 6/1997 | Simmen | 433/37 |
| 5,733,118 | A | 3/1998 | Pankuch | 433/38 |
| 5,820,372 | A | 10/1998 | Jones | 433/38 |
| D413,386 | S | 8/1999 | Werrin | D24/181 |
| 5,975,906 | A | 11/1999 | Knutson | 433/226 |
| 5,989,700 | A | 11/1999 | Krivopal | 428/323 |
| 6,244,864 | B1 * | 6/2001 | Fujiwara et al. | 433/71 |
| 6,450,808 | B1 | 9/2002 | Pelerin | 433/38 |
| 6,835,065 | B1 | 12/2004 | Wise | 433/38 |
| 7,021,929 | B2 | 4/2006 | DiMarino | 433/38 |
| 7,101,178 | B2 | 9/2006 | Diesso | 433/37 |
| 7,101,179 | B2 | 9/2006 | Liddle | 433/38 |

OTHER PUBLICATIONS

Stean, Howard May 1993 PTFE Tape:"A Versatile Material in Restorative Dentistry," Dental Update, vol. 20, No. 4, pp. 146-148.
3M Company packaged a polyethylene impression "SPACER" sheet with "Express" silicone impression putty system for the purpose of shimming space to form a phase one impression.

* cited by examiner

*Primary Examiner*—Ralph A Lewis (57) ABSTRACT

Processes wherein a soft polymer sheet deforms readily under the pressure of dental surfaces brought into contact with one another. As such, the sheet does not itself interfere with such contact. Processes for the sheet include deforming the sheet between contacting dental surfaces, and noting the location and intensity of contact deformations. The position of the sheet is stabilized on the surfaces by temporary adhesion, wherein the adhered sheet does not interfere with contact. Further processes involve deforming the sheet between contacting dental surfaces such that the sheet does not interfere with the contact of the dental surfaces, and utilizing the sheet to support dental materials, such as supporting restorative composite, impression materials, and so on. The sheet is preferably comprised of polytetrafluoroethylene.

2 Claims, 10 Drawing Sheets

SOFT POLYMER DENTAL SHEET AND PROCESSES THEREFOR

FIELD OF THE INVENTION

The present invention relates to dentistry, specifically to materials interposed between contacting dental surfaces.

BACKGROUND OF THE INVENTION

Materials interposed between contacting dental surfaces, such as occluding dental arches, tend to interfere with the proper contact of the surfaces. Characteristics inherent with these materials, such as thickness and resistance to deformation, prevent the dental surfaces from contacting properly.

For occluding surfaces, the materials further interfere with proper contact of the teeth by triggering neuromuscular proprioceptive responses, which tend to pull the jaw away from centric occlusion when interferes are encountered.

Procedures which utilize materials interposed between contacting dental surfaces include interference marking, occlusal registration, dual arch impressions for indirect restorations, molding of composites, and so on.

For the descriptions contained herein, general references to "teeth" include any dental restorations or prostheses thereof, including but not restricted to: fillings, inlays, onlays, veneers, crowns, bridges, partial or full denture teeth, and restored implants. General references to "appliances" include guards, splints, stents, retainers, and partial or full dentures, and so on.

Interference Marking

Interfering contacts between teeth, restorations, or appliances, are typically disclosed by marking with inked articulating paper. It is intended that the contact pressure transfers the ink onto the teeth.

However, inks and papers tend to create many false positive and false negative marks because they mark where they shouldn't, and don't mark where they should. In addition, the thickness of the paper can interfere with proper contact, such as occlusion, or seating restorations and appliances. As a result, dentists waste time trying to locate the actual interferences, and sometimes inadvertently relieve valuable dental structure.

Other marking systems involve painting ink or indicating paste to the surfaces of the teeth, restorations, or appliances, and the contact pressure and friction then removes the ink. These are subject to problems similar to those of the ink papers.

Another method of marking interferences involves interposing a PTFE strip between the luting surface of an indirect restoration, including crowns, inlays, and onlays, and the prepared surfaces of a tooth. However, general use PTFE strips are fragile and difficult to use. They are also less reliable as an interference indicator when not adhered, due to inadvertent repositioning with respect to the dental surface upon which it rests.

Molding Restorative Materials

Multiple methods are used to shape hardenable restorative materials, such as composites, in cavity preparations which oppose appliances.

For a first method, the composite is hardened first. The composite is then fitted to the appliance by trial and error abrasion. This method is time consuming, and the fit of the composite to the appliance is frequently poor.

For a second method, the appliance is seated against the composite prior to hardening, so the appliance directly shapes the composite. The fit of the composite to the appliance is good. However the composite sometimes locks the appliance onto the restored tooth.

For a third method, a plastic sheet is interposed between the unhardened composite and the appliance such that the composite is shimmed away from locking undercuts. However, the plastic sheet is likely to interfere with proper seating of the appliance, and tends to form an irregular composite surface.

Occlusal Registration

Occlusal registrations record the locations, and sometimes the relative force, of occlusal contact areas of the teeth. Occlusal registrations are used for the fabrication of crowns, bridges, prostheses and appliances, as well as record the patient's occlusal status during occlusal therapy or TMJ therapy.

Materials currently used for occlusal registration include impression materials, wax wafers, and electronic sensors. While the impression materials typically do not interfere with proper occlusion, they are costly, and long-term storage is difficult due to their fragility and bulkiness. Some waxes can cause occlusal interference, and are difficult to store due to temperature sensitivity and fragility. While electronic sensors permit digital storage, and indicate relative occlusal contact forces in the z-axis, they are costly, and can interfere with proper occlusion.

Dual Arch Impressions

Trays used for dual arch impressions have a peripheral frame connected to a thin central membrane for supporting impression material. With one impression sequence, dual arch trays acquire impressions of either arch, as well as an occlusal registration.

The membrane is generally comprised of gauze materials of minimal thickness and rigidity, such that interference to the occlusion of the teeth is minimized. However, the membrane causes a degree of interference to proper occlusion.

Two Phase Impressions

The detail captured by dental impressions is improved when a closely fitting tray increases the hydraulic pressure of the impression material, and thereby drives the impression material into smaller spaces. A method for forming closely fitting trays involves taking a preliminary, or phase one, impression prior to the final, or phase two, impression. The phase one impression can thereby function as a closely fitted custom tray for the phase two impression.

A first method for forming a phase one impression is to interpose a plastic sheet between the impression material and the teeth before seating the impression tray over the teeth. The sheet reserves a small space over the surface of the phase one impression. During the phase two impression, the reserved space reduces interferences to reseating the phase one impression back over the teeth. The reserved space also provides an escape for the flowing phase two impression material displaced by the occluding teeth. This reduces excessive pressure of the flowing phase two impression material against the set phase one impression material, and thereby reduces distortion of the phase one impression material. Substantial distortion of the phase one impression during the phase two impression can in turn elastically distort the phase two impression after removal from the teeth.

Spacing phase one impressions with the plastic spacer sheet method is generally used for single-arch impression trays only. However, interposing a substantially non-deformable plastic sheet between the teeth and the impression material on a dual arch tray would interfere with the proper occlusion of the teeth.

A second method for forming a phase one impression is to manually relieve the surface of the phase one impression with a large bur, to create space for the phase two impression material. However, this is time consuming and inexact.

A third method for forming a phase one impression is to make the phase one impression having no relief spacing, but create a hole through the impression in the vicinity of the prepared tooth. The phase two impression is formed by partly loosening the phase one impression from the teeth, injecting phase two impression material through the hole, and reseating the teeth into the injected impression material until cured.

OBJECTS AND ADVANTAGES

It is an object of the present invention to provide a substantially deformable sheet useful for convenient placement and removal of onlays and inlays from tooth preparations to facilitate forming interference indicating marks.

It is an object of the present invention to provide a substantially deformable sheet useful for adhering to dental surfaces for marking dental interferences, wherein said sheet will not cause substantial interference to the occlusion.

It is yet a further object of the present invention to provide a substantially deformable sheet useful for isolating and molding uncured composite restorative material, wherein said sheet will not cause substantial interference to seating a dental appliance.

It is thus an object of the present invention to provide a substantially deformable sheet useful for recording contacting points of the dental arches, wherein said sheet is compact, may be scanned into a computer for analysis, and will not cause substantial interference to the occlusion.

It is an object of the present invention to provide a substantially deformable support sheet useful for supporting impression material in a dual arch impression tray, wherein said support membrane will not cause substantial interference to the occlusion.

It is a further object of the present invention to provide a substantially deformable spacer sheet useful for spacing phase one, dual arch impressions, wherein said spacer sheet will not cause substantial interference to the occlusion.

SUMMARY OF THE INVENTION

The processes of the invention utilize an polymeric sheet comprised of a dead soft polymeric material, having low shape memory, and suitable for the following uses: pressure indicator, matrix, separator, barrier, support sheet, and container.

It is preferred that the sheet is semi-opaque, but has sufficient translucency to permit partial transmission of dental curing light. However, the sheet is effective over a range of opacity.

The preferred soft polymer sheet is porous, expanded polytetrafluoroethylene, or PTFE, (DUPONT) sheeting, strip, or tape, made from a precursor unsintered PTFE ranging from 0.7-1 g/cc, but preferring 0.9 g/cc. Preferred specifications for the PTFE include a thickness ranging from 80 to 85 microns, expanded within a range of 85% to 115%, wherein a typical pore measures 3 microns wide by 20 microns long, with pores having a wide range of sizes, and having a blue tint to facilitate transmission of composite curing light wavelengths, and for identification. However, other sheet specifications for width, length, thickness, density, expansion, pore size, color, and polymeric composition, such as other fluoroethylene polymers, can be effective.

In contrast to the W.L. Gore tetrafluoroethylene polymers, expansion rates, temperatures, and percentages preferred for the present invention enjoy a wider range of tolerances. In addition, post-expansion annealing to increase crystallinity does not preserve preferred sheet properties. To the knowledge of Applicant, PTFE is not currently or routinely manufactured to the preferred specifications. It is the opinion of Applicant that PTFE tapes available in plumbing stores are substantially inferior for performance of the dental processes described in this application, as well as for other dental procedures. As such, Applicant believes that various specifications of soft polymer material are marketable in dentistry. In addition, special preparation may be indicated for oral use, such as gas sterilization, which would further differentiate it from commonly available PTFE tapes.

The sheet is useful for certain dental procedures involving contacting dental surfaces because the sheet deforms readily under pressure. Under pressure, the sheet thickness is readily compressed to a fraction of the original thickness. The sheet is dead soft, so it does not substantially rebound after compression. Substantially, the sheet permits seating of dental restorations and appliances. Similarly, the sheet permits proper occlusion of the dental arches, and does not interfere with occlusion of the teeth.

REFERENCE NUMERALS IN DRAWINGS

| 20 | sheet | 22 | marks |
| 24 | extension | 26 | adhesive |
| 28 | appliance | 30 | restorative |
| 32 | frame | 34 | tray |
| 36 | impression material | 38 | full arch tray |

DETAILED DESCRIPTION OF THE DRAWINGS

The following description of the present invention is illustrative only and not in any way limiting. Other embodiments and uses of the invention will readily suggest themselves to those of ordinary skill in the art.

According to the present invention, various embodiments and uses of a sheet are disclosed which extend the accuracy, convenience, and economy of various dental procedures which involve contacting dental surfaces.

Figure 1A:
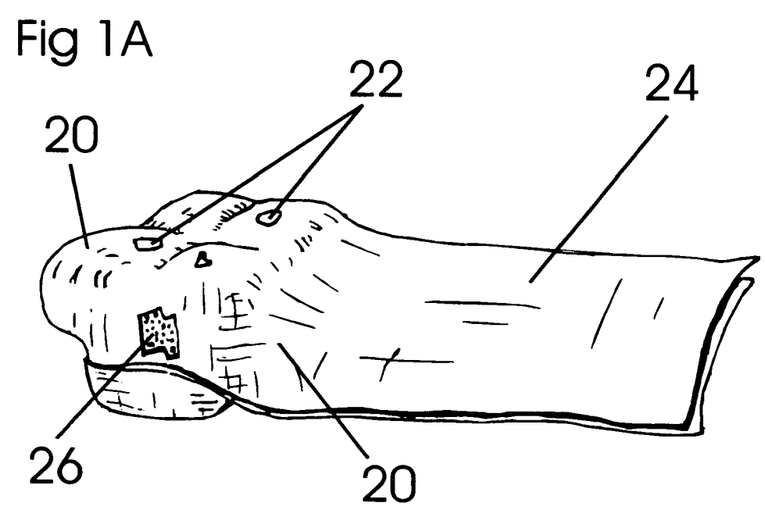
FIGS. 1A and 1B are perspective views of a sheet covering an onlay, and showing interference marks.
Figure 1B:
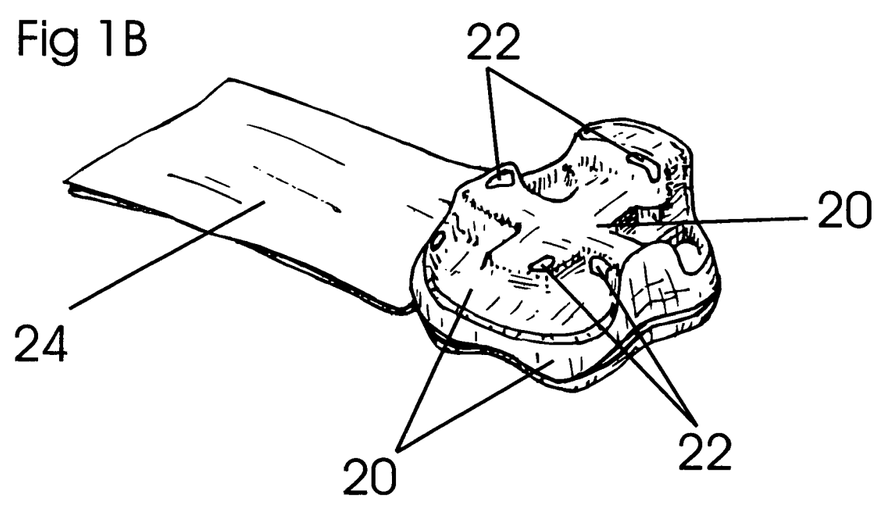

FIGS. 1A and 1B are perspective views of a sheet 20 covering an onlay after forceful seating on a prepared tooth. As the onlay is seated into the preparation, sheet 20 deforms to facilitate seating of the onlay onto the prepared tooth. Pressure at seating interference points deforms sheet 20, such that the thickness of sheet 20 is substantially reduced, or thinned, at the interference points. The thinned areas of sheet 20, marks 22, do not substantially rebound, and have a degree of transparency. The degree of transparency is relative to the amount of pressure. Marks 22 generally appear dark, and are distinct from the white of sheet 20.

While the onlay is seated in the preparation, the opposing teeth may be occluded against sheet 20 to form marks 22, and thereby indicate occlusal interferences.

Sheet 20 is folded over the onlay such that the onlay is covered by the central portion of the length of sheet 20. Both ends of sheet 20 extend away from the onlay. The ends are superimposed over one another to form an extension, extension 24. Extension 24 forms a purchase for secure gripping the onlay during transportation to and from the tooth preparation for interference marking. The size of the sheet 20 segment is sufficiently large to cover the onlay and form extension 24.

It is preferred that a temporary adhesive, adhesive 26, (Tapetrix Adhesive, Novadent) shown in a cutaway, is applied to onlay surfaces prior to application of sheet 20, such that the position of sheet 20 is stabilized on the surfaces of the onlay, thereby enhancing the correlation between the location of onlay interferences and the location of marks 22. As such, marks 22 tend to have positional stability, such that they remain over the actual interference point of the onlay, rather than shifting away from the interference. As such, marks 22 reliably indicate fitting interferences on sheet 20.

Figure 2:
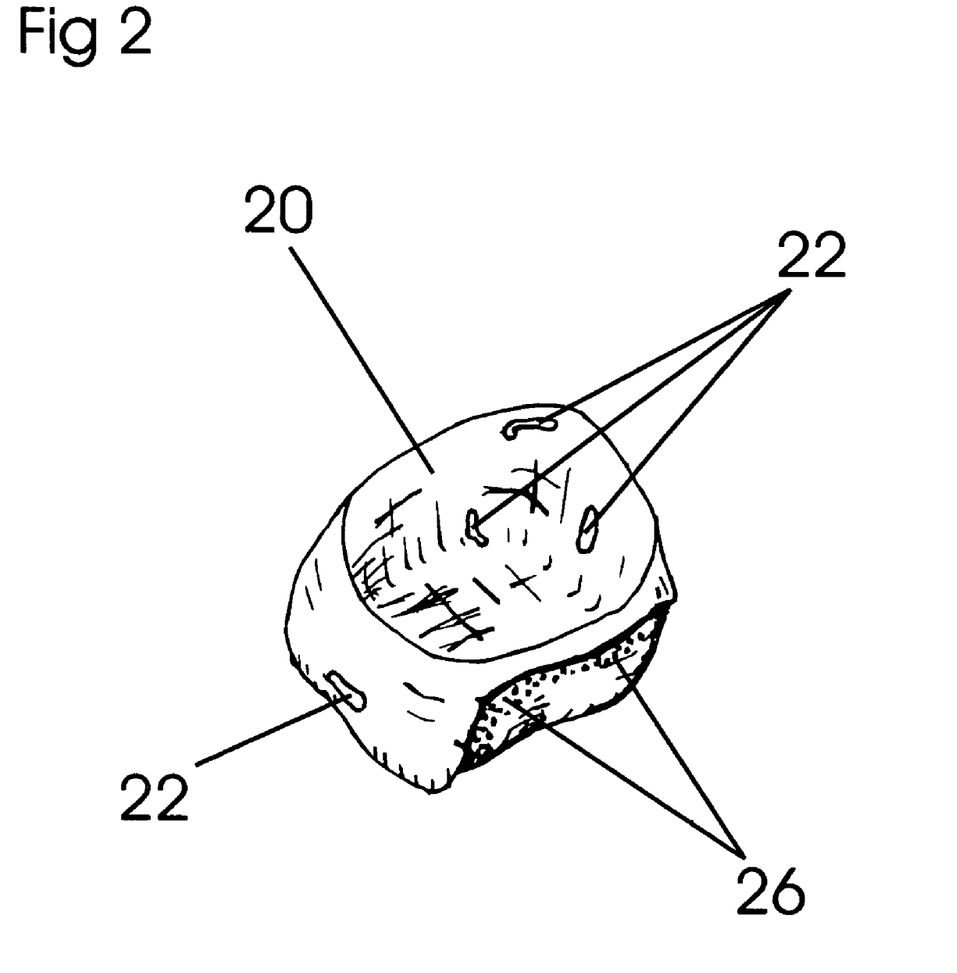
FIG. 2 is a perspective view of a sheet adhered to a crown showing interference marks.

FIG. 2 shows a sheet 20 mounted on the internal and interproximal surfaces of a crown, after forceful seating of the crown on a prepared tooth. The seating has formed seating interference marks 22 on sheet 20. Sheet 20 deforms to facilitate seating of the crown onto the prepared tooth.

It is preferred that a temporary adhesive, adhesive 26, is applied to the surfaces of the crown prior to application of sheet 20, such that the position of sheet 20 is stabilized on the surfaces of the crown, thereby enhancing the correlation between the location of crown interferences and the location of marks 22.

Figure 3:
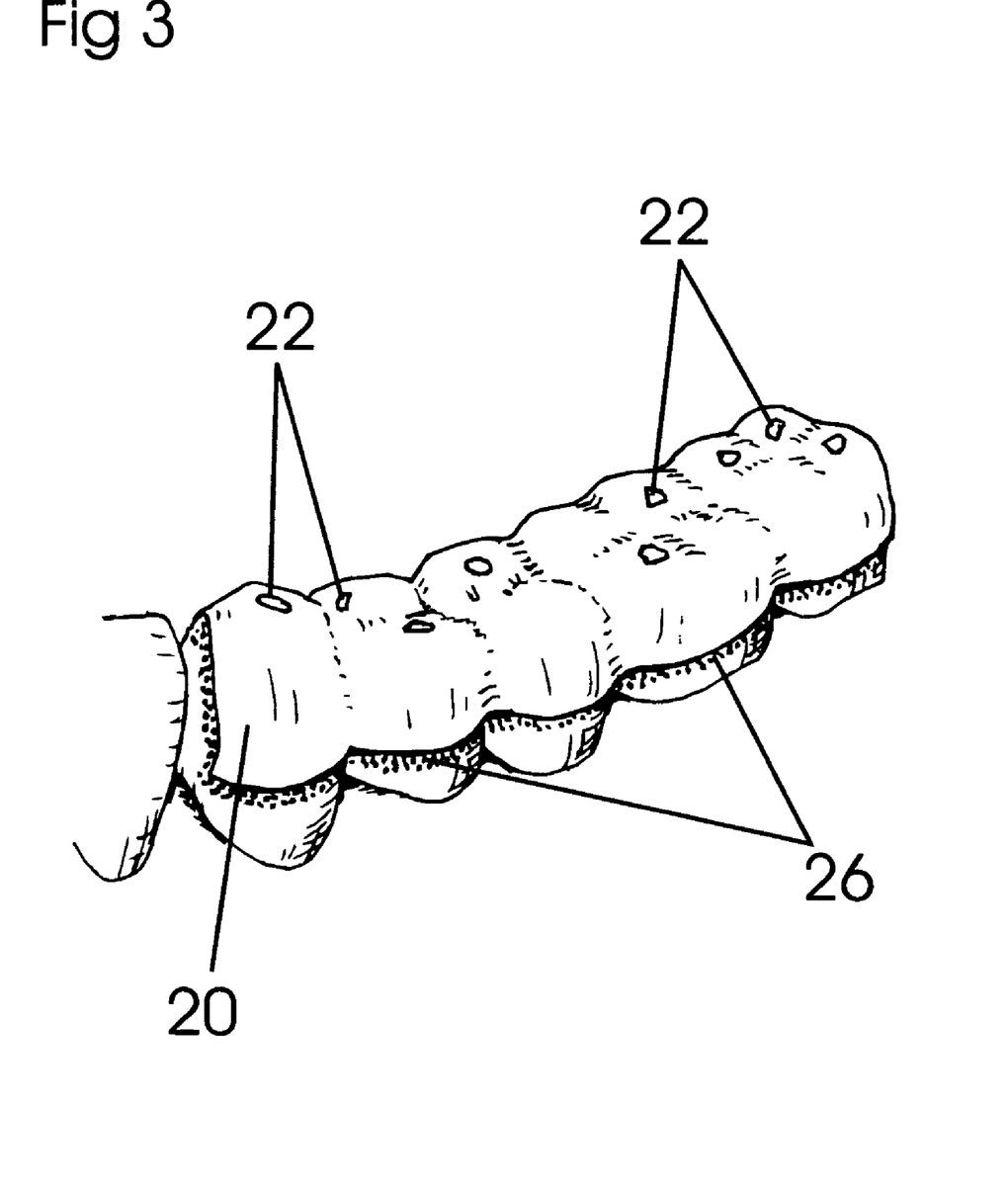
FIG. 3 is a perspective view of a sheet showing occlusal contact marks while mounted on an arch for indicating occlusal interferences.

FIG. 3 shows sheet 20 mounted on teeth after forceful occlusion of the teeth with the opposing arch has formed occlusal contact marks 22 on sheet 20. As such, sheet 20 indicates the occlusal contacts. Sheet 20 deforms to facilitate proper occlusion of the teeth.

It is preferred that adhesive 26 is applied to the surfaces of the teeth prior to application of sheet 20, such that the position of sheet 20 is stabilized on the teeth, thereby enhancing the correlation between the location of occlusal interferences and the location of marks 22.

Figure 4:
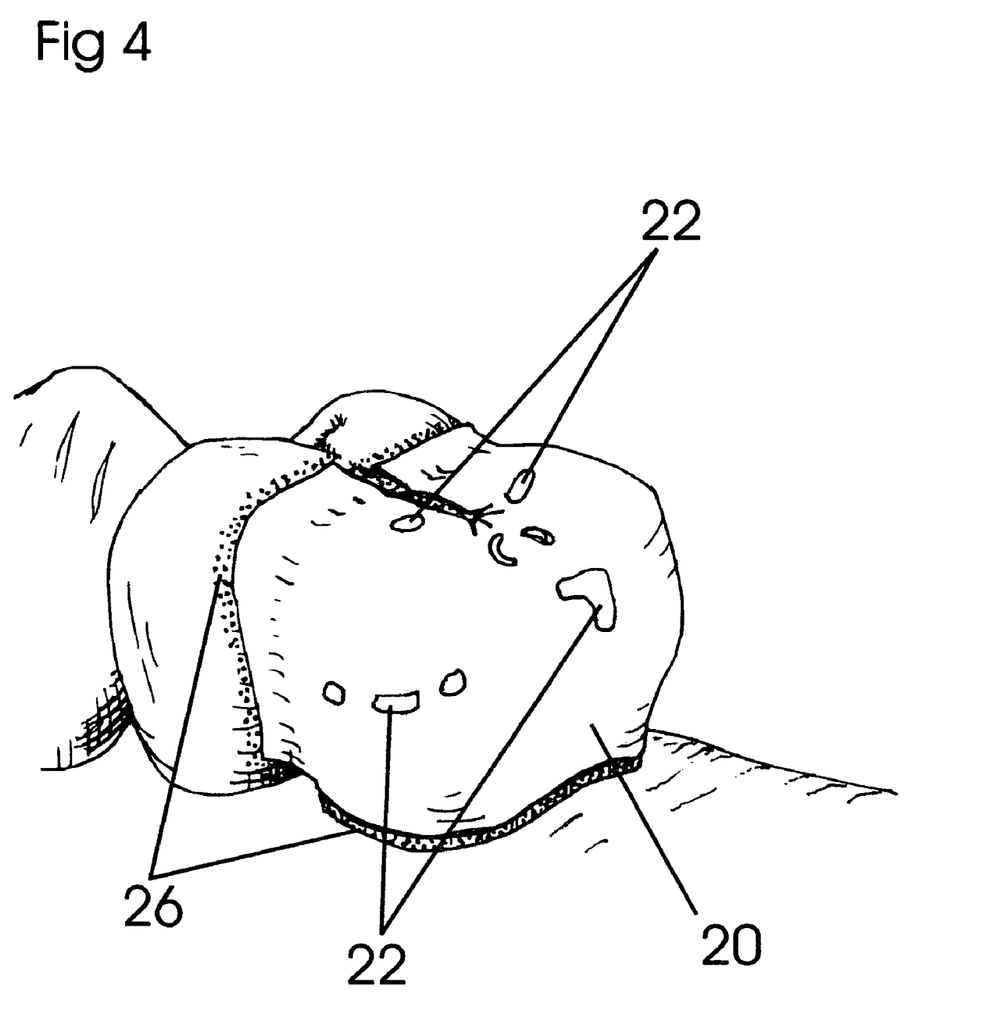
FIG. 4 is a perspective view of a sheet adhered to a tooth showing interference marks from seating an appliance and from occlusion.

FIG. 4 shows sheet 20 mounted on a tooth or crown after forcefully seating of a partial denture, or other dental appliance, thereby forming seating interference marks 22 on sheet 20. Sheet 20 deforms to facilitate seating of the appliance onto the tooth or crown. Marks 22 shown are typical following contact with an occlusal rest, a guide-plane, a clasp, and opposing teeth.

It is preferred that adhesive 26 is applied to the surfaces of the tooth or crown prior to application of sheet 20, such that the position of sheet 20 is stabilized on the teeth.

Figure 5:
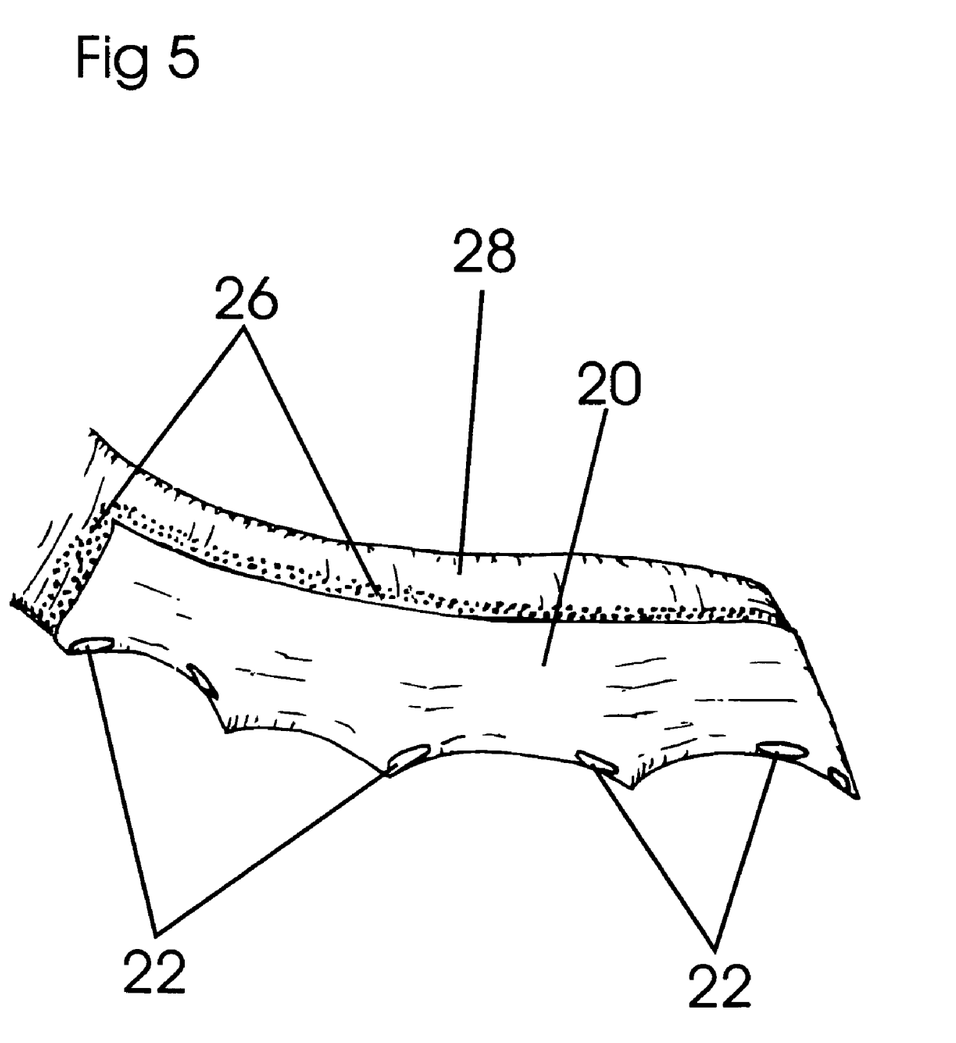
FIG. 5 is a perspective view of a sheet adhered to a dental appliance showing interference marks.

FIG. 5 shows sheet 20 mounted to a dental appliance, appliance 28, such as a partial denture, after forceful seating on the teeth has formed marks 22 on sheet 20. Sheet 20 deforms to facilitate seating of appliance 28 onto the teeth.

It is preferred that adhesive 26 is applied to the surfaces of appliance 28 prior to application of sheet 20, such that the position of sheet 20 is stabilized on the teeth.

Figure 6:
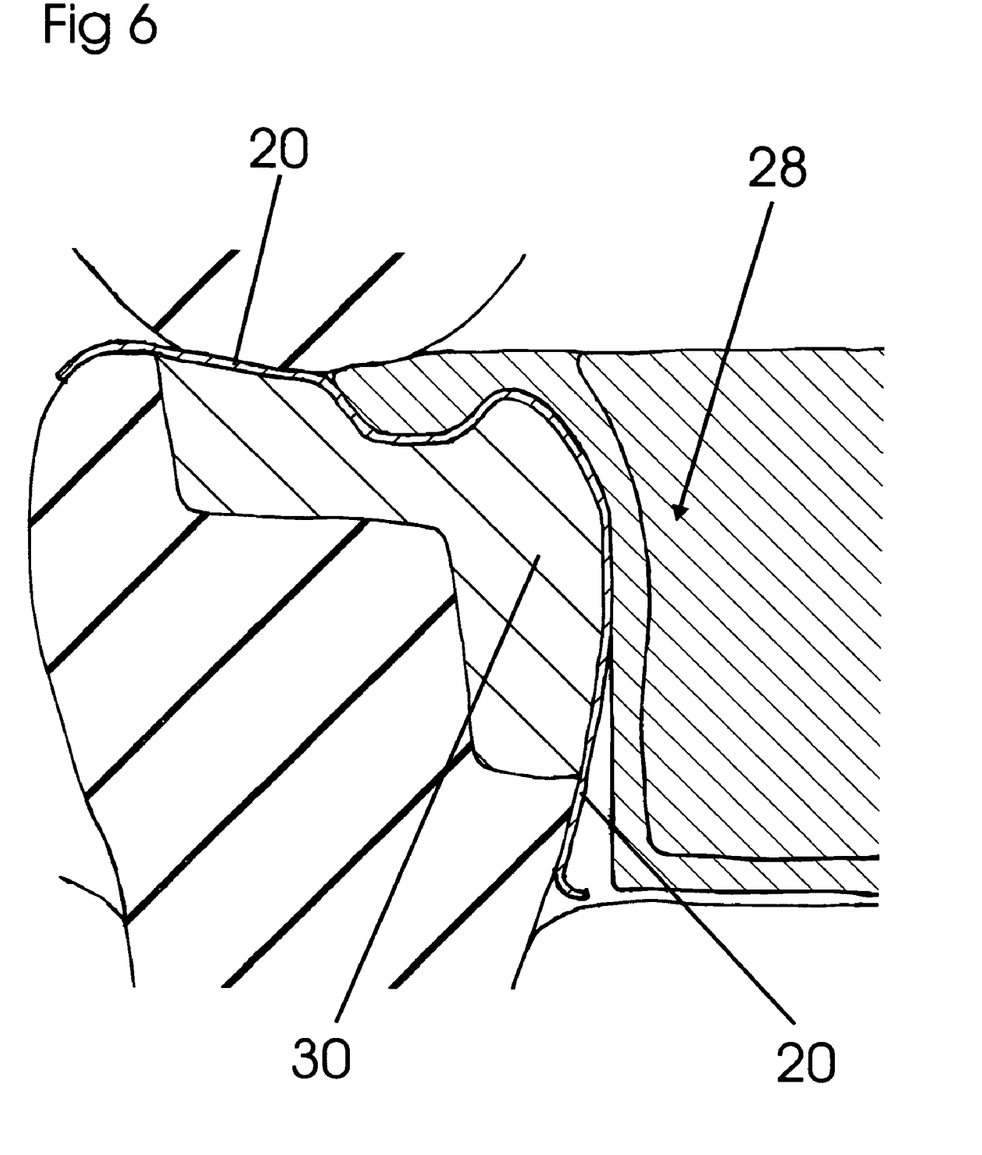
FIG. 6 is a cross-sectional view of a sheet used as a deformable separator during molding of uncured restorative material.

FIG. 6 shows a sheet 20 covering unhardened restorative material, restorative 30, in a tooth. An appliance 28 is shown seated against sheet 20 and the tooth. Sheet 20 deforms to facilitate seating of appliance 28 onto the tooth. As appliance 28 presses against sheet 20, it shapes sheet 20. Appliance 28 thereby molds restorative 30 to fit appliance 28. A tooth of the opposing arch is shown occluding against sheet 20 and appliance 28, such that the opposing tooth further shapes sheet 20 and restorative 30.

It is preferred that adhesive 26 is applied to the surfaces of the tooth or crown prior to application of sheet 20, such that the position of sheet 20 is stabilized on the teeth.

Figure 7:
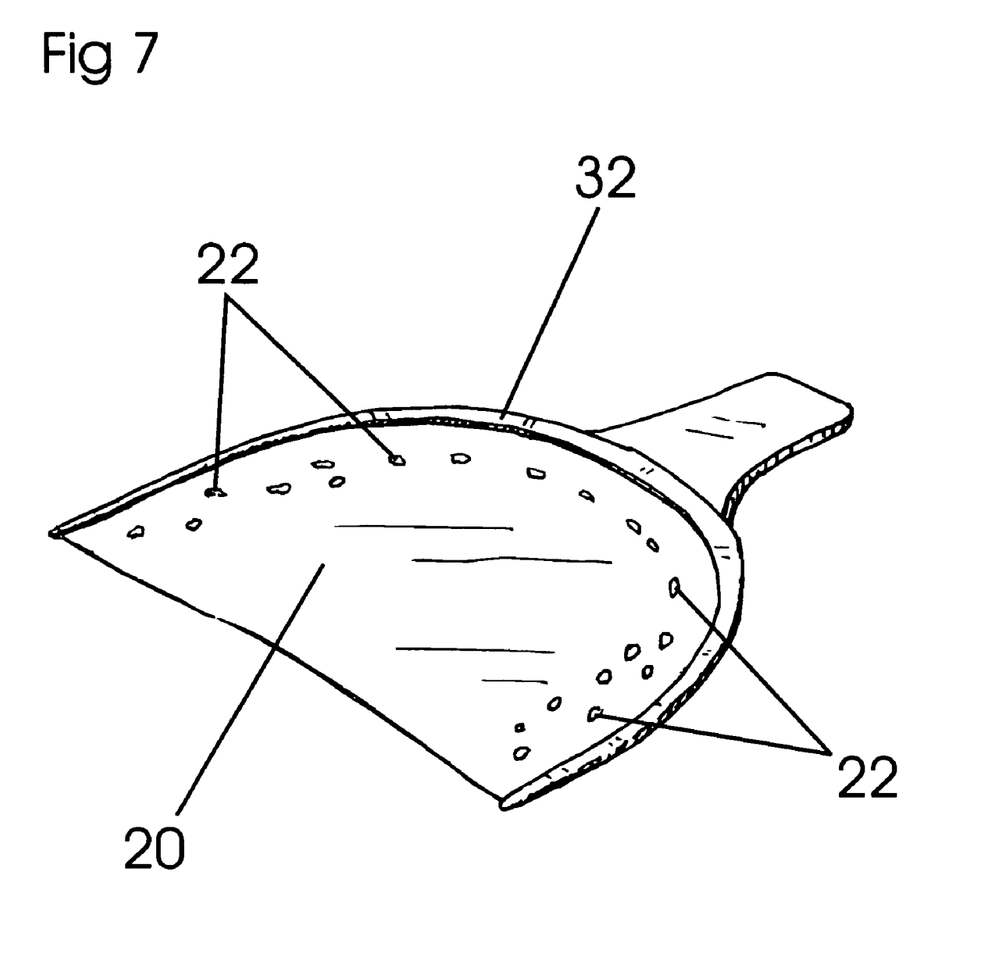
FIG. 7 is a perspective view of a frame connected to a sheet having occlusal marks for occlusal registration.

FIG. 7 shows a sheet 20 after forceful occlusion of the teeth has formed occlusal registration marks 22 on sheet 20. An occlusal registration frame, frame 32, connects to sheet 20.

It is preferred that frame 32 is thin, to facilitate compact storage. It is also preferred that frame 32 is flexible to facilitate insertion into a narrow mouth. However, frame 32 may have substantial thickness and rigidity. Frame 32 may be detachable from sheet 20, such as a frame 32 comprising a spring-loaded clip having upper and lower mating halves.

Figure 8:
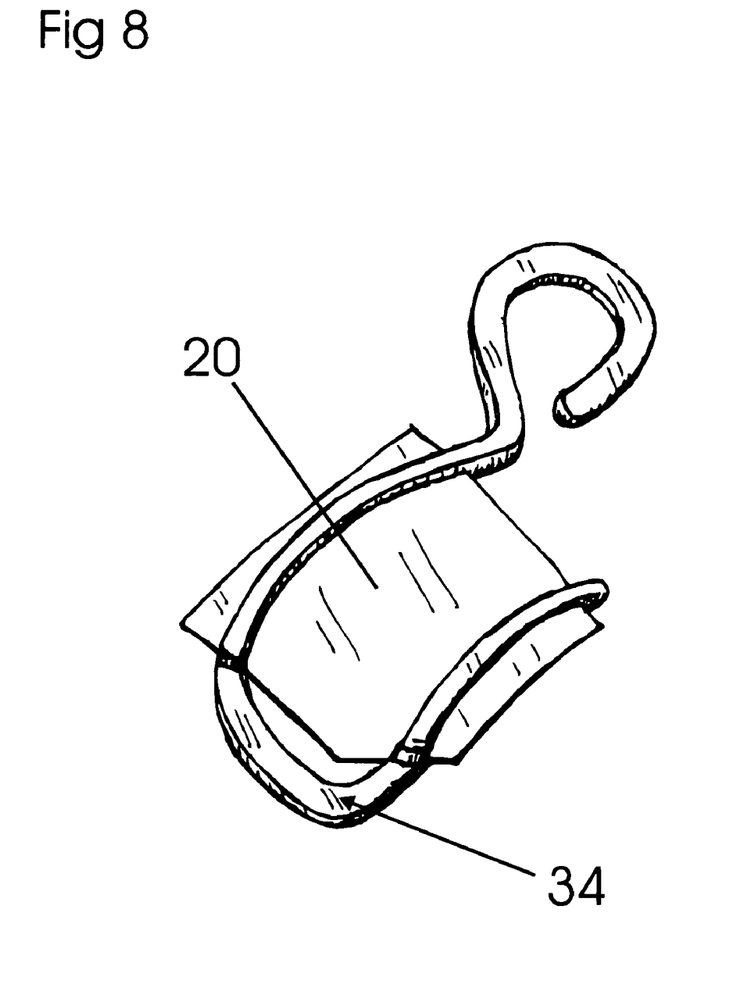
FIG. 8 is a perspective view of a sheet connected to a tray for supporting impression material.

FIG. 8 shows sheet 20 connected to a dual arch tray, tray 34. Sheet 20 is ready to be loaded with, and support, impression material for taking an impression. Sheet 20 supports the impression material, and tray 34 supports sheet 20. During the impression, the upper and lower dental arches will occlude through the impression material, and into sheet 20. During occlusion, sheet 20 deforms to facilitate proper occlusion of the dental arches.

Figure 9:
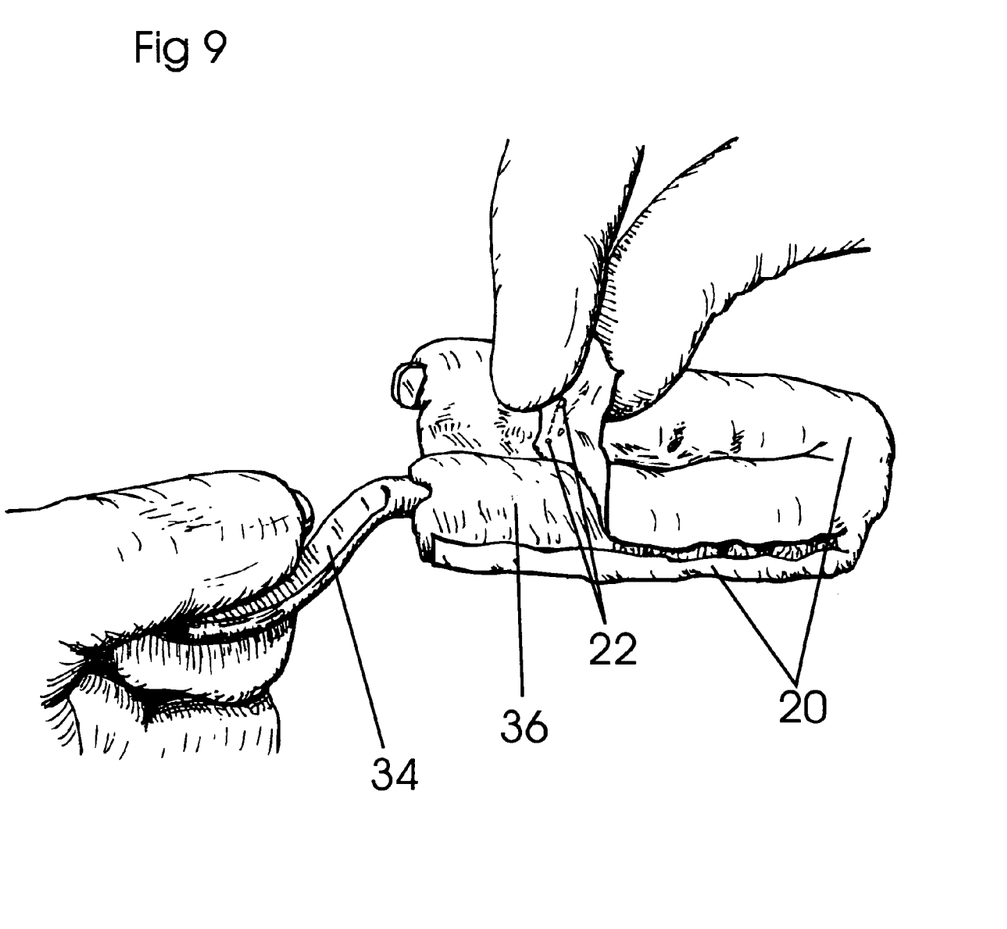
FIG. 9 is a perspective view of a sheet being removed after spacing an impression.

FIG. 9 shows removal of a sheet 20 from covering a phase one impression. Sheet 20 is covering cured impression material, impression material 36, thereby forming a phase one impression. Prior to impression material 36 curing, opposing arches of teeth occluded on sheet 20 and on impression material 36. Sheet 20 and impression material 36 are on both sides of tray 34. As such, sheet 20 has reserved a relief space in the phase one impression that will be useful for a phase two impression. During occlusion, sheet 20 deformed to facilitate proper occlusion of the teeth, as indicated by marks 22 formed thereby.

Figure 10:
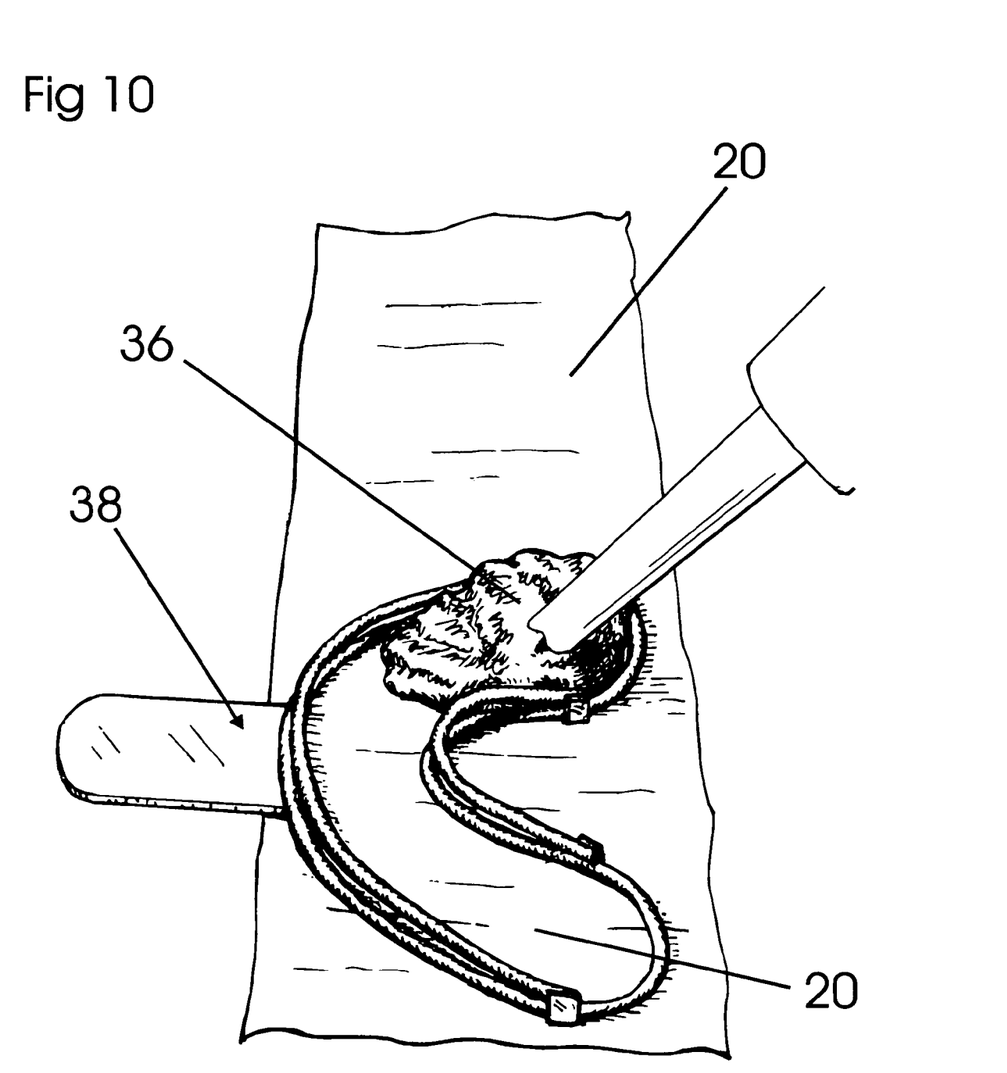
FIG. 10 is a perspective view of a sheet being loaded with impression material prior to taking an impression with a full arch tray.

FIG. 10 shows a sheet 20 lying under a full arch dual arch impression tray (D&D Impression Trays, Superior Dental), full arch tray 38, as sheet 20 is loaded with impression material 36. Full arch tray 38 is open in the center, and does not have a connected central supporting membrane.

After loading, sheet 20 will be interposed between occluding arches of teeth and the uncured impression material 36 in full arch tray 38 to form a phase one impression. As such, sheet 20 will reserve a relief space in the phase one impression that will be useful for a phase two impression. During occlusion, sheet 20 deforms to facilitate proper occlusion of the teeth.

From the description above, a number of advantages of sheet 20 become evident:

(a) For marking seating interferences, inlays and onlays can be securely transported to a prepared tooth in a segment of sheet 20 sufficiently large to extend beyond the restoration.

(b) When adhered to teeth, crowns, bridges, appliances 28, and so on, sheet 20 can reliably mark occlusal and seating interferences.

(c) A sheet 20 connected to a frame 32 can conveniently and accurately record the occlusal contacts of the dental arches, can be scanned for computer input, and can be stored compactly.

(d) A sheet 20 covering a moldable restorative 30 in a tooth readily deforms to permit seating of an appliance 28 against the tooth, such that the seated appliance 28 shapes sheet 20, and thereby molds restorative 30.

(e) A sheet 20 connected across the central area of a tray 34 can support impression material 36 without substantially interfering with the occlusion of the teeth.

(f) A sheet 20 interposed between occluding teeth and impression material 36 can reserve space in an impression without substantially interfering with the occlusion of the teeth.

Operation—FIGS. 1-10

By using the deformable sheet of the invention, it is now possible, surprisingly, to interpose a sheet between contacting dental surfaces without substantially interfering with proper contact thereof.

The sheet offers the advantage that the user can now quickly record contacts and interferences, take dental impressions, and shape composite fillings with increased accuracy and predictability.

EXAMPLE 1

For marking seating interferences of onlays, or inlays, a 7 cm length of 18 mm width sheet 20 is cut from a spool (Novadent). Sheet 20 is laid flat on a worksurface, wherein the length of sheet 20 has a first half and a second half. A dab of adhesive 26 is dispensed onto a mixing pad.

An onlay is partly coated with adhesive 26 using a gauze square, to enhance stability of sheet 20 relative to the surface of the onlay. The onlay is placed on the first half of sheet 20, adjacent to the midpoint of the length of sheet 20. The onlay is oriented such that the buccal surface of the onlay is toward the end of the first half of sheet 20. The second half of sheet 20 is folded over the first half, such that sheet 20 covers the onlay. Each of the ends of the sheet 20 halves are brought together, to form a handle, extension 24. Any excess sheet 20 width is folded toward, and pressed onto, the occlusal surface of the onlay to prevent the excess sheet 20 from interfering with seating the onlay.

Extension 24 is grasped, and the onlay is thereby transported to, and forcefully seated into, the tooth preparation. Onlay interference points press into sheet 20 to form marks 22. The onlay is removed from the tooth by grasping extension 24. Marks 22 indicate the location of seating interferences, as shown in FIG. 1. The onlay is adjusted by abrading the onlay through sheet 20 at marks 22, such as with a diamond bur.

EXAMPLE 2

For fitting crowns, sheet 20 is useful for marking interferences on all surfaces. To mark internal and interproximal seating interferences on crowns, including onlays, and veneers, user cuts a 20 mm long segment of 18 mm width sheet 20 from a spool. A dab of adhesive 26 is dispensed onto a mixing pad.

A brush is dipped into the adhesive 26, and used to lightly coat adhesive 26 onto the internal crown surface. The interproximal surface of the crown is touched to adhesive 26, such that adhesive 26 is transferred to, and coats, the crown surface. The adhesive 26 coated crown surface is touched to the segment of sheet 20, near one end of the segment. Sheet 20 is pressed onto the interproximal surface of the crown with a finger. The remainder of sheet 20 is pushed up inside the crown to cover the internal surfaces, such as with a brush, and smoothed to minimize wrinkles. Sheet 20 is thereby adhered to the crown.

The crown is forcefully seated on the prepared tooth to mark interferences. Sheet 20 deforms to facilitate seating the crown on the tooth, and to form marks 22. The crown is removed from the tooth. Substantially, there are no false positive marks 22, and all significant contacts or interferences form marks 22, as shown in FIG. 2. Marks 22 show internal and interproximal interferences. The interferences are adjusted at marks 22 by abrading with a diamond bur through sheet 20, while sheet 20 remains adhered to the crown. Sheet 20 is removed from the crown, and adhesive 26 is sandblasted or wiped from the crown with a cotton swab.

To mark interferences on the interproximal or occlusal surfaces of a crown, user cuts several 12 mm long segments of 10 mm width sheet 20 from a spool (Novadent). The sheet 20 segments are laid out on the mixing pad.

The interproximal or occlusal surface of the crown is touched to adhesive 26, such that adhesive 26 is transferred to, and coats, the crown surface. The adhesive 26 coated crown surface is touched to a sheet 20 segment, thereby adhering the sheet 20 segment to the crown. The sheet 20 segment is pressed onto the crown with a finger, or cotton roll.

The crown with the adhered sheet 20 segment is seated on the prepared tooth. To mark interproximal interferences, the crown is forcefully seated on the prepared tooth. To mark the occlusal interferences, the opposing teeth are forcefully occluded against sheet 20. Sheet 20 deforms to permit proper seating or occlusion, and to form marks 22. The crown is removed from the tooth, and the interferences are indicated by marks 22. The interfering contacts are adjusted by abrading with a stone or diamond bur while sheet 20 remains adhered to the crown. Sheet 20 is removed from the crown, and adhesive 26 is wiped from the crown with a gauze square.

EXAMPLE 3

To mark occlusal contacts on teeth, user cuts a 4 cm long segment of 12 mm width sheet 20 from a spool (Novadent). The sheet 20 segment is placed in an articulating paper holder.

The teeth are isolated with cotton rolls and dried thoroughly. Adhesive 26 is applied to the teeth with a gauze square. Sheet 20 is placed over the adhesive 26-coated teeth. Sheet 20 is pressed onto the teeth with a finger or cotton roll, and released from the articulating paper holder.

The teeth are forcefully occluded against sheet 20. Sheet 20 deforms under the pressure of the occlusal contacts to permit proper occlusion of the teeth. Sheet 20 does not cause substantial interference to the occlusion. The patient discludes the teeth, and occlusal contacts are visible as marks 22, as shown in FIG. 3. Substantially, there are no false positive marks, and all significant contacts are marked. Sheet 20 has marked the occlusal contacts.

User identifies the darkest and largest mark 22 as the location of an interfering occlusal contact. The contact is adjusted by abrading at mark 22 with a diamond bur while sheet 20 remains adhered to the tooth. Sheet 20 is removed from the teeth, and adhesive 26 is wiped from the teeth with a gauze square.

EXAMPLE 4

To fit an appliance 28 to a tooth or crown, user cuts a 25 mm long segment of 10 mm width sheet 20 from a spool. Adhesive 26 is applied to the tooth or crown surface, such as with a gauze square. The sheet 20 segment is touched onto the adhesive 26 coated tooth surface, and pressed onto the tooth surface, thereby adhering the sheet 20 segment to cover the tooth.

Appliance 28 is seated on the teeth. Sheet 20 deforms to facilitate seating, and to form marks 22 at the seating interferences. Appliance 28 is removed from the teeth. The interferences are indicated by marks 22, as shown in FIG. 4. The interference is adjusted by abrading with a stone or diamond bur at marks 22 while sheet 20 remains adhered to the tooth. Sheet 20 is removed from the tooth, and adhesive 26 is wiped off with a gauze square.

To further fit an appliance 28 to a tooth, user cuts a 40 mm long segment of 12 mm width sheet 20 from a spool. Adhesive 26 is applied to the interfering surfaces of appliance 28, such as with a gauze square. The sheet 20 segment is adhered to appliance 28, minimizing folds.

Appliance 28 is seated on the teeth. Sheet 20 deforms to facilitate seating, and to form marks 22 at the seating interferences. Appliance 28 is removed from the tooth, and the interferences are indicated by marks 22, as shown in FIG. 5. The interferences are adjusted by abrading with a stone, diamond bur, or acrylic bur at marks 22 while sheet 20 remains adhered to appliance 28. Sheet 20 is removed from appliance 28, and adhesive 26 is wiped off with a gauze square.

EXAMPLE 5

A tooth cavity is prepared for a filling, wherein the cavity preparation at least partly involves an interproximal surface which is opposed by an appliance 28, such as a partial denture. Uncured restorative 30, such as composite, is placed into the cavity preparation. Adhesive 26 is applied to the tooth surfaces about the preparation. A 12 mm long segment of sheet 20 is cut from a 10 mm width spool. Sheet 20 is placed to cover the composite, as well as the adhesive coated tooth surfaces.

Appliance 28 is seated onto the teeth, and against sheet 20 covering restorative 30. Sheet 20 deforms to facilitate seating of appliance 28 Appliance 28 presses against sheet 20, and shapes sheet 20 to fit appliance 28. As such, sheet 20 shapes restorative 30 to fit appliance 28. The teeth may be occluded onto the seated appliance 28, to further shape sheet 20, and restorative 30 therewith, to fit the occluding teeth, as shown in FIG. 6. In addition, sheet 20 shims restorative 30 slightly away from appliance 28, thereby increasing the chance that appliance 28 will be readily removable from the teeth after restorative 30 is hardened.

A curing light is directed toward the buccal surfaces of the prepared tooth to initiate curing of restorative 30. The teeth are discluded, and restorative 30 is cured further by directing the curing light through sheet 20. Appliance 28 is removed, and restorative 30 is cured further. Sheet 20 is removed, and restorative 30 is cured, contoured and polished.

EXAMPLE 6

For registering the occlusion of the teeth, user selects a full arch frame 32 and connected sheet 20.

Sheet 20 and frame 32 are inserted into a patient's mouth. The patient forcefully occludes the teeth in proper occlusion on sheet 20. Sheet 20 does not cause substantial interference to the occlusion, and deforms to permit proper occlusion of the teeth, forming marks 22. The patient discludes, and frame 32 and sheet 20 is removed and inspected, as shown in FIG. 7.

The occlusal marks 22 are sharply visible against white sheet 20. Substantially, there are no false positive marks, and all significant contacts are marked. Sheet 20 has formed an occlusal registration of all the significant occlusal contact points of the dental arches.

The details of each mark 22 also reveal information regarding individual occlusal contacts. Each point of a mark 22 has a unique degree of translucency, proportional to the amount of pressure from the contact. The greater the pressure, the more translucent the point of mark 22. Therefore, a first point of an individual mark 22 may have a different translucency than a second point Sheet 20 is autoclaved, and then placed on a scanner. A black sheet is placed behind sheet 20 for contrast, and sheet 20 is digitally scanned into a computer. The computer records the locations and size of marks 22, as well as the relative grayscale intensities of marks 22. The relative intensities of each mark 22 may be assigned relative occlusal pressures to the individual marks 22. Thereby, the z-axis pressure values for individual marks 22 are definable. Sheet 20 is placed in an envelope for compact storage.

EXAMPLE 7

To make a quadrant dual arch impression tray, tray 34, having a sheet 20 supporting membrane, a 40 mm long segment of 40 mm width sheet 20 is cut from a spool (Novadent). Opposing edges of the sheet 20 segment are threaded into slits in the opposing members of a tray 34. The slits are compressed to hold sheet 20, such that sheet 20 is connected to tray 34. Excess sheet 20 is trimmed away. As such, a tray 34 having a sheet 20 supporting membrane is made, as shown in FIG. 8.

To form a phase one, dual arch impression, a 12 cm long segment of sheet 20 is cut from a 50 mm width spool (Novadent) for use as a spacer sheet. Both sides of tray 34 with a sheet 20 supporting membrane are loaded with impression material 36. The 12 cm long sheet 20 segment spacer sheet is wrapped around both sides of impression tray 34, such that spacer sheet 20 substantially covers impression material 36 on either side of tray 34.

Tray 34 is inserted between opposing arches of teeth. The teeth are occluded against, and readily deform both spacer sheet 20 and supporting sheet 20, as well as the uncured impression material 36. As such, the opposing arches of teeth properly occlude.

In addition, because sheet 20 readily deforms and stretches, spacer sheet 20 displaces a minimum of phase one impression material 36. The resulting phase one impression fits the teeth more closely than impressions spaced with plastic sheets. The improved fit increases the fluid pressure achieved during a phase two impression.

The phase one impression material 36 is allowed to cure, thereby forming a phase one impression, and removed from the teeth. Spacer sheet 20 is removed from the outer surface of the impression, as shown in FIG. 9. Sheet 20 has reserved space for reseating the impression on the teeth without interferences, and for additional uncured impression material 36 during the phase two impression.

To form the phase two impression, uncured impression material 36 is added to either side of the cured phase one impression. Tray 34 is inserted between the opposing arches of teeth. The teeth readily occlude through the uncured phase two impression material 36, and reseat into the imprint of the phase one impression. The small space which was previously reserved by sheet 20 facilitates reseating of the teeth into the phase one impression imprint without interference.

The small space reserved by sheet 20 also provides backpressure in the phase two impression material 36. The pressure is not excessive, so as to avoid distorting of the phase one impression, which would in turn distort the phase two impression. However, the pressure is sufficient to drive the phase two impression material 36 into the gingival sulcus, and other detailed spaces about the teeth.

The phase two impression material 36 is allowed to cure. As such, the resulting quadrant phase two impression is highly detailed, and is substantially free of distortion.

EXAMPLE 8

To form a full arch, dual arch impression, an 18 cm long segment of 7.5 cm width sheet 20 is cut from a spool (Novadent), and laid flat on a work surface. The length of sheet 20 has a first half and a second half. A full-arch tray 38 is set on the first half of the length of sheet 20, and oriented with the tray handle toward a side of sheet 20.

Sheet 20 is loaded with uncured impression material 36 inside the perimeter of full arch tray 38, as shown in FIG. 10. The second half of sheet 20 is folded back over the top of the uncured impression material 36 and the full arch tray 38, such that sheet 20 covers both the top and bottom of full arch tray 38. For convenience, the loose edges of sheet 20 are pressed against the full arch tray 38 perimeter, out of the way. The full arch tray 38 with sheet 20 and the uncured impression material 36 is inserted into a patient's mouth. Sheet 20 supports the uncured impression material 36 during transport to the mouth.

The teeth are occluded against, and readily deform, sheet 20 and the uncured impression material 36. As such, the opposing arches of teeth properly occlude. The impression material 36 is allowed to cure to form a full arch, dual arch, phase one impression. The full arch tray 38 is removed from the mouth, and sheet 20 is peeled off the surface of the cured impression material 36, forming a. Sheet 20 has reserved a space for phase two impression material 36, and for seating of the phase one impression onto the teeth without interferences.

To form a phase two impression, uncured impression material 36 is loaded onto either side of the phase one impression. The phase one impression with uncured impression material 36 is inserted between the opposing arches of teeth. The teeth readily occlude through the uncured phase two impression material 36, and seat into the imprint of the spaced, phase one impression.

The small space reserved by sheet 20 facilitates reseating of the teeth into the phase one impression imprint without interference, and creates backpressure for the phase two impression material 36. As such, the impression material 36 records detail without causing substantial distortion in the phase one impression. The impression material 36 is allowed to cure to form a phase two impression. As such, the full arch, phase two impression is highly detailed, and is substantially free of distortion.

SUMMARY, RAMIFICATIONS, & SCOPE

Accordingly, the reader will see that the sheet of this invention can improve a number of dental procedures which involve contacting dental surfaces.

Substantially, sheet 20 permits proper occlusion of the dental arches, and does not interfere with occlusion of the teeth. Sheet 20 can support, contain, or separate dental materials while permitting proper occlusion of the teeth, and the seating of dental restorations and appliances 28. Furthermore, the sheet has an additional advantage in that it consistently forms highly contrasted marks 22 at points of contact, such as interferences or occlusal contacts.

Although the description above contains many specificities, these should not be construed as limiting the scope of the invention and process, but as merely providing illustrations of some of the presently preferred embodiments of this invention.

For a first example, an appliance 28, such as a removable partial denture, may be substituted for a tray 34 in a phase one impression for a new abutment crown. A first half of a length of sheet 20 is laid under appliance 28 in the area of the clasp for the prepared tooth. Impression material 36 is loaded over appliance 28 and sheet 20, and then covered with a second half of sheet 20. Appliance 28, with sheet 20 and impression material 36, is seated onto the teeth, and the teeth are occluded until impression material 36 cures to form a phase one impression. The phase two impression is then taken over the phase one impression.

For a second example, phase one impressions using single-arch trays may be spaced with sheet 20. Impression material 36 is loaded into a single-arch impression tray, and a segment of sheet 20 sufficiently large to cover the tray is laid over impression material 36 and the tray. The tray is seated onto an arch of teeth, and held until impression material 36 is cured, forming a single arch, phase one impression.

For a third example, phase one impressions may be made with only sheet 20 supporting impression material 36, and with no rigid tray providing additional support.

I claim:

1. A process for determining a dental contact area between two dental objects, wherein said contact area comprises a first surface area portion of a first dental object that contacts a second surface area of a second dental object, comprising the steps of:
    applying a thin coating of a temporary adhesive to said first surface area of said first dental object,
    adhering a thin sheet of dead soft polymeric material having a low shape memory to the adhesively coated first dental surface area so that it substantially conforms to the shape of the first dental surface area
    contacting said second surface area of said second dental object against the adhered polymeric sheet such that the adhered polymeric sheet is deformed to form a visible mark over said contact area, and
    determining where contact has occurred between the first and second dental objects from the visible mark formed in the deformed polymeric sheet.

2. The process of claim 1, wherein said polymeric sheet is comprised of polytetrafluoroethylene.

* * * * *